US012172676B2

United States Patent
Nakanishi et al.

(10) Patent No.: US 12,172,676 B2
(45) Date of Patent: Dec. 24, 2024

(54) INFORMATION PROCESSING DEVICE, INFORMATION PROCESSING SYSTEM, PROGRAM, AND VEHICLE

(71) Applicant: TOYOTA JIDOSHA KABUSHIKI KAISHA, Toyota (JP)

(72) Inventors: Tooru Nakanishi, Nagakute (JP); Tadashi Yamada, Toyota (JP); Josuke Yamane, Nissin (JP); Mitsuhiro Miura, Toyota (JP); Tomo Sasaki, Toyota (JP); Tomoyuki Kozuka, Toyota (JP); Tae Sugimura, Miyoshi (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 236 days.

(21) Appl. No.: 17/218,454

(22) Filed: Mar. 31, 2021

(65) Prior Publication Data
US 2021/0370979 A1 Dec. 2, 2021

(30) Foreign Application Priority Data
May 28, 2020 (JP) .................. 2020-093175

(51) Int. Cl.
*B60W 60/00* (2020.01)
*G01C 21/34* (2006.01)
(Continued)

(52) U.S. Cl.
CPC ..... *B60W 60/0025* (2020.02); *G01C 21/3484* (2013.01); *G05D 1/0088* (2013.01);
(Continued)

(58) Field of Classification Search
CPC ....... B60W 60/0025; B60W 2540/215; B60W 2540/049; B60W 2540/221; G16H 40/67;
(Continued)

(56) References Cited

U.S. PATENT DOCUMENTS 7,835,859 B2 * 11/2010 Bill .................... G01C 21/3617
340/995.13
8,108,083 B2 * 1/2012 Kameyama ............ G16H 50/30
701/538
(Continued)

FOREIGN PATENT DOCUMENTS

CN 108873887 A 11/2018
JP 4085738 B2 * 5/2008
(Continued)

OTHER PUBLICATIONS

"Todd, Ryan; Evaluating Traveler Preferences, Values, and Behaviors Associated with Public Rest Areas; 2013; SAGE Publications; Transportation Research Record vol. 2358, Issue 1: Highway Design" (Year: 2013).*
(Continued)

*Primary Examiner* — Elaine Gort
*Assistant Examiner* — Christopher R Cardimino
(74) *Attorney, Agent, or Firm* — Oblon, McClelland, Maier & Neustadt, L.L.P.

(57) ABSTRACT

An information processing device includes a control unit. The control unit acquires biometric information and occupant information of an occupant of a vehicle, estimates state information of the occupant based on the acquired biometric information, and compares the estimated state information and the acquired occupant information with past data for another occupant in which the state information and the occupant information are associated with facility information of a service facility used, to determine a service facility fit for the occupant.

16 Claims, 8 Drawing Sheets

(51) Int. Cl.
  G05D 1/00 (2024.01)
  G06N 5/04 (2023.01)
  G06Q 50/14 (2012.01)
  G16H 40/20 (2018.01)
  G16H 40/67 (2018.01)
  G16H 50/30 (2018.01)

(52) U.S. Cl.
  CPC ............... G06N 5/04 (2013.01); G06Q 50/14 (2013.01); G16H 40/20 (2018.01); G16H 40/67 (2018.01); G16H 50/30 (2018.01); *B60W 2540/049* (2020.02); *B60W 2540/215* (2020.02); *B60W 2540/221* (2020.02); *G06Q 2240/00* (2013.01)

(58) Field of Classification Search
  CPC .... G16H 40/20; G16H 50/30; G01C 21/3484; G05D 1/0088; G06N 5/04; G06Q 50/14; G06Q 2240/00
  See application file for complete search history.

(56) References Cited

U.S. PATENT DOCUMENTS

| | | | |
|---|---|---|---|
| 9,457,814 B2* | 10/2016 | Kim | B60W 50/0097 |
| 9,884,629 B2* | 2/2018 | Gordon | A61B 5/6893 |
| 9,937,792 B2* | 4/2018 | Nania | G01C 21/362 |
| 10,372,129 B1* | 8/2019 | Urmson | G06V 20/58 |
| 10,609,148 B1* | 3/2020 | Tran | G06Q 50/40 |
| 11,267,482 B2* | 3/2022 | Monteil | A61B 5/389 |
| 11,292,477 B2* | 4/2022 | el Kaliouby | A61B 5/4803 |
| 2007/0010942 A1 | 1/2007 | Bill | |
| 2017/0057516 A1 | 3/2017 | Gordon et al. | |
| 2017/0355377 A1* | 12/2017 | Vijaya Kumar | B60W 50/0098 |
| 2018/0335776 A1* | 11/2018 | Theis | B60W 50/082 |

FOREIGN PATENT DOCUMENTS

| | | |
|---|---|---|
| JP | 4509042 B2 | 7/2010 |
| JP | 5181741 B2 | 4/2013 |
| JP | 2014-240777 A | 12/2014 |
| JP | 2018195311 A * | 12/2018 |
| JP | 2019-119342 A | 7/2019 |
| JP | 2019-127238 A | 8/2019 |

OTHER PUBLICATIONS

"Verbert, K; Context-Aware Recommender Systems for Learning: A Survey and Future Challenges; Oct. 2012; IEEE Transactions On Learning Technologies, vol. 5" (Year: 2012).*

* cited by examiner

FIG. 3

| VEHICLE | OCCUPANT INFORMATION | STATE INFORMATION | SERVICE FACILITY |
|---|---|---|---|
| A1 | ONE ADULT MALE | DEGREE OF DROWSINESS: 90 | CAPSULE HOTEL |
| A2 | TWO ADULTS, TWO CHILDREN | DEGREE OF DROWSINESS: 90 | FAMILY-FRIENDLY HOTEL |
| A3 | ONE ADULT FEMALE | DEGREE OF FATIGUE: 90 | MASSAGE SHOP |
| A4 | TWO ADULTS | DEGREE OF LACK OF EXERCISE: 90 | FITNESS CLUB |
| ... | ... | ... | ... |

FIG. 4

| VEHICLE | OCCUPANT INFORMATION | STATE INFORMATION | FACILITY INFORMATION |
|---|---|---|---|
| B1 | ONE ADULT FEMALE | DEGREE OF FATIGUE: 90 | INFORMATION OF MASSAGE SHOP |
| B2 | ONE ADULT MALE | DEGREE OF DROWSINESS: 85 | INFORMATION OF CAPSULE HOTEL |
| B3 | THREE ADULTS | DEGREE OF LACK OF EXERCISE: 90 | INFORMATION OF FITNESS CLUB |
| B4 | TWO ADULTS, ONE CHILD | DEGREE OF DROWSINESS: 90 | INFORMATION OF FAMILY-FRIENDLY HOTEL |
| ... | ... | ... | ... |

FIG. 5

| VEHICLE | STATE INFORMATION | AUTONOMOUS DRIVING STATE INFORMATION |
|---|---|---|
| C1 | DEGREE OF DROWSINESS: 90 | LOW SPEED, LOW ACCELERATION |
| C2 | DEGREE OF FATIGUE: 90 | LOW ACCELERATION |
| C3 | DEGREE OF LACK OF EXERCISE: 90 | SPEED LIMIT |
| ... | ... | ... |

INFORMATION PROCESSING DEVICE, INFORMATION PROCESSING SYSTEM, PROGRAM, AND VEHICLE

CROSS-REFERENCE TO RELATED APPLICATION

This application claims priority to Japanese Patent Application No. 2020-093175 filed on May 28, 2020, incorporated herein by reference in its entirety.

BACKGROUND

1. Technical Field

The present disclosure relates to an information processing device, an information processing system, a program, and a vehicle.

2. Description of Related Art

A technique for acquiring and managing biometric information of an occupant of a vehicle has been known. For example, Japanese Patent No. 5181741 (JP 5181741 B) discloses a biometric information generation device that generates biometric information in accordance with the situation of each occupant and transmits the biometric information itself and determination results of the occupant's physical condition to an information processing device installed in a medical institution for use in medical practice.

SUMMARY

In the related art, the biometric information generation device has a main purpose of generating biometric information for use in medical practice. In JP 5181741 B in which the biometric information generation device is disclosed, it is not sufficiently considered to optimize the service facility to be proposed to the occupant of the vehicle based on the biometric information of the occupant.

An object of the present disclosure made in view of such circumstances is to make it possible to optimize the service facility to be proposed to the occupant of the vehicle based on the biometric information of the occupant.

An information processing device according to an aspect of the present disclosure includes a control unit that acquires biometric information and occupant information of an occupant of a vehicle, estimates state information of the occupant based on the acquired biometric information, and compares the estimated state information and the acquired occupant information with past data for another occupant in which the state information and the occupant information are associated with facility information of a service facility used, to determine a service facility fit for the occupant.

A program according to an aspect of the present disclosure causes an information processing device to perform operations including: acquiring biometric information and occupant information of an occupant of a vehicle; estimating state information of the occupant based on the acquired biometric information; comparing the estimated state information and the acquired occupant information with past data for another occupant in which the state information and the occupant information are associated with facility information of a service facility used; and determining a service facility fit for the occupant.

A vehicle according to an aspect of the present disclosure includes a control unit that acquires biometric information and occupant information of an occupant of the vehicle, estimates state information of the occupant based on the acquired biometric information, and compares the estimated state information and the acquired occupant information with past data for another occupant in which the state information and the occupant information are associated with facility information of a service facility used, to determine a service facility fit for the occupant.

The information processing device, the information processing system, the program, and the vehicle according to the aspects of the present disclosure enable optimization of the service facility to be proposed to the occupant of the vehicle based on the biometric information of the occupant.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 3 is a first diagram illustrating a first example of a process executed by a control unit of the information processing device shown in FIG. 2;

FIG. 4 is a second diagram illustrating the first example of the process executed by the control unit of the information processing device shown in FIG. 2;

FIG. 5 is a diagram illustrating a second example of the process executed by the control unit of the information processing device shown in FIG. 2;

DETAILED DESCRIPTION OF EMBODIMENTS

Hereinafter, embodiments of the present disclosure will be described below with reference to the drawings.

Figure 1:
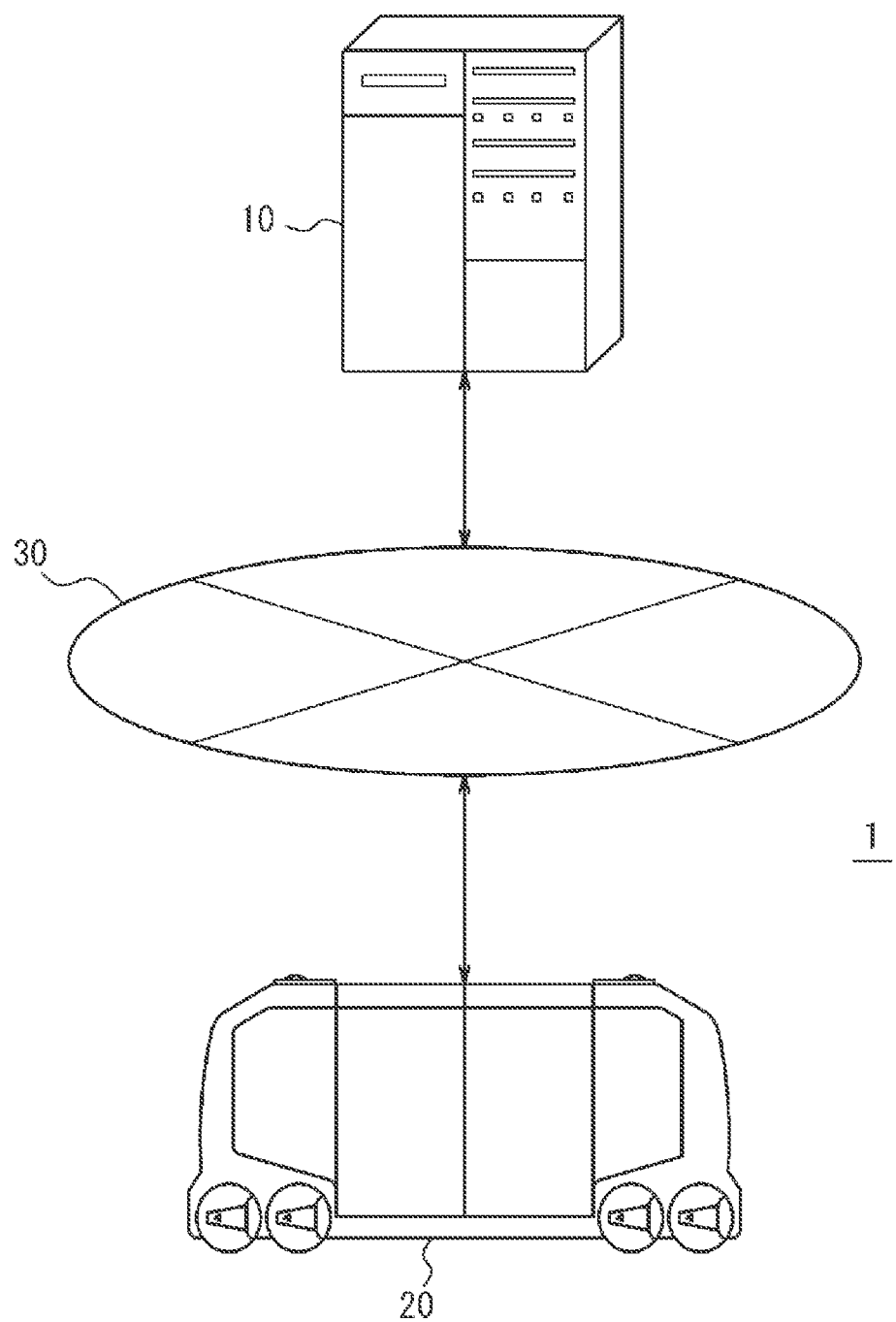
FIG. 1 is a configuration diagram showing a configuration of an information processing system including an information processing device according to an embodiment of the present disclosure.

FIG. 1 is a configuration diagram showing a configuration of an information processing system 1 including an information processing device 10 according to an embodiment of the present disclosure. An outline of the information processing system 1 including the information processing device 10 according to the embodiment of the present disclosure will be mainly described with reference to FIG. 1. The information processing system 1 includes a vehicle 20 in addition to the information processing device 10.

For convenience of description, FIG. 1 shows a single information processing device 10 and a single vehicle 20. However, the numbers of the information processing devices 10 and the vehicles 20 included in the information processing system 1 may be two or more. For example, an occupant may continuously use the same vehicle 20, or may use any one of a plurality of the vehicles 20 while changing the vehicle 20 for each riding or by a predetermined period. Each of the information processing device 10 and the vehicle 20 is connected to a network 30 including a mobile communication network and the Internet, for example, so as to be able to communicate with each other.

The information processing device 10 is a server or a plurality of servers that can communicate with each other. The information processing device 10 is not limited to the above, and may be any general-purpose electronic device such as a personal computer (PC) or a smartphone, or may be another electronic device dedicated to the information processing system 1.

The vehicle 20 is, for example, an automobile. The vehicle 20 is not limited to this, and may be any vehicle that allows a human to board and drive to a destination. The vehicle 20 is, for example, a vehicle that performs autonomous driving. Autonomous driving includes, for example, Levels 1 to 5 defined by the Society of Automotive Engineers (SAE). However, autonomous driving is not limited to the above, and may be appropriately defined. The vehicle 20 is not limited to the vehicle that performs autonomous driving, and may be any vehicle driven by a driver.

As an outline of the embodiment, the information processing device 10 acquires biometric information and occupant information of the occupants of the vehicle 20. In the present specification, the "biometric information" includes the biological state of the occupant including, for example, electroencephalogram, cerebral blood flow, blood pressure, blood glucose level, blood amino acid, heart rate, pulse, body temperature, and sensible temperature. In the present specification, the "occupant information" includes, for example, the number, ages, genders, weights, physiques, clothes, races, conversation content, boarding times, behavior, and the like of the occupants. The number of occupants of the vehicle 20 may be one or more.

The information processing device 10 estimates state information of the occupants of the vehicle 20 based on the acquired biometric information. In the present specification, the "state information" includes, for example, a degree of drowsiness, a degree of fatigue, a degree of lack of exercise, a degree of hunger, and the like of the occupant. The state information may be expressed based on any index. For example, the state information may be represented by a numerical value within any numerical range. For example, the state information may be represented by a numerical value from 0 to 100. At this time, the larger the value of the state information, the greater the degree of the state information of the occupant. On the contrary, the smaller the value of the state information, the smaller the degree of the state information of the occupant. The state information is not limited to these, and may be represented by any of three levels, for example, "high", "medium", and "low".

The information processing device 10 compares the estimated state information and the acquired occupant information with past data for other occupants in which the state information and the occupant information are associated with facility information of the service facility used. Thereby, the information processing device 10 determines a service facility fit for the occupant of the vehicle 20. In the present specification, the "service facility" includes facilities that provide services related to health, healing, accommodation, entertainment, food and beverage, and the like. In the present specification, the "facility information of the service facility" includes, for example, information on the location, type, and equipment of the service facility. In the present specification, the "past data" includes, for example, big data in which state information and occupant information obtained in the past in relation to other occupants who boarded each of the vehicles 20 are associated with the facility information of the service facility that each of the other occupants used.

Figure 2:
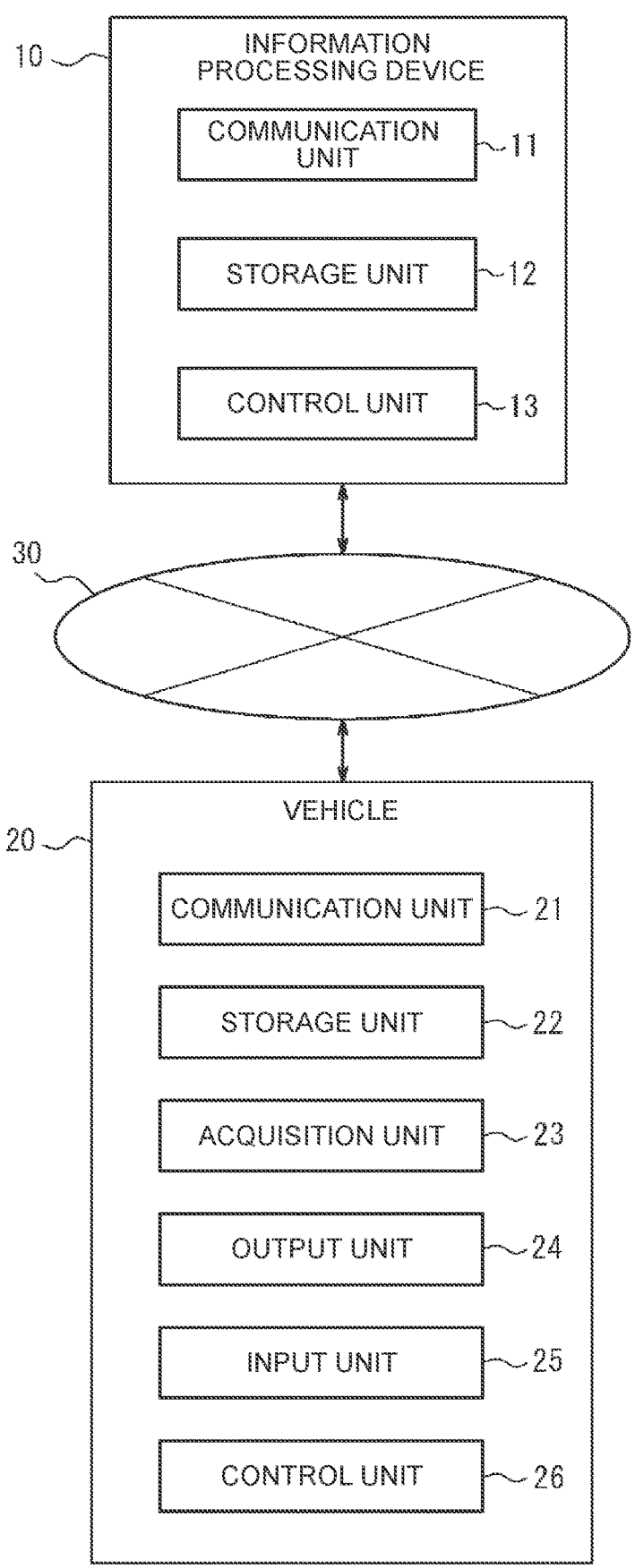
FIG. 2 is a functional block diagram showing a schematic configuration of each of the information processing device and a vehicle shown in FIG. 1.

Next, with reference to FIG. 2, configurations of the information processing device 10 and the vehicle 20 included in the information processing system 1 will be mainly described. FIG. 2 is a functional block diagram showing a schematic configuration of each of the information processing device 10 and the vehicle 20 shown in FIG. 1.

As shown in FIG. 2, the vehicle 20 includes a communication unit 21, a storage unit 22, an acquisition unit 23, an output unit 24, an input unit 25, and a control unit 26. The communication unit 21, the storage unit 22, the acquisition unit 23, the output unit 24, the input unit 25, and the control unit 26 are connected to each other so as to be able to communicate with each other via an in-vehicle network such as a controller area network (CAN) or a dedicated line.

The communication unit 21 includes a communication module connected to the network 30. For example, the communication unit 21 may include a communication module corresponding to a mobile communication standard such as the fourth generation (4G) and the fifth generation (5G). According to the embodiment, the vehicle 20 is connected to the network 30 via the communication unit 21. The communication unit 21 transmits and receives various types of information via the network 30.

The storage unit 22 is, for example, a semiconductor memory, a magnetic memory, or an optical memory. However, the storage unit 22 is not limited to these memories. The storage unit 22 may function as, for example, a main storage device, an auxiliary storage device, or a cache memory. The storage unit 22 stores any information used for operation of the vehicle 20. For example, the storage unit 22 stores the biometric information and the occupant information of the occupant acquired by the acquisition unit 23. In addition, for example, the storage unit 22 may store a system program, an application program, and various types of information received by the communication unit 21. The information stored in the storage unit 22 may be updatable with information received from the network 30 via the communication unit 21, for example.

The acquisition unit 23 includes any module capable of acquiring the biometric information of the occupant of the vehicle 20. For example, the acquisition unit 23 includes a sensor module capable of acquiring various biometric information described above. The acquisition unit 23 includes any module capable of acquiring the occupant information of the occupant of the vehicle 20. For example, the acquisition unit 23 includes a seating sensor installed in a seat of the vehicle 20 such as a driver's seat, a passenger seat, and a rear seat in which an occupant is seated. For example, the acquisition unit 23 includes a camera module, a microphone, and any other sensor module installed in the vehicle cabin of the vehicle 20 and connected to the CAN.

In addition, the acquisition unit 23 may include one or more receivers corresponding to any satellite positioning system. For example, the acquisition unit 23 may include a global positioning system (GPS) receiver. The acquisition unit 23 acquires a measured value of the position of the vehicle 20 as the position information. The position information includes, for example, an address, latitude, longitude, and altitude. The acquisition unit 23 may acquire the position information of the vehicle 20 constantly or may acquire the position information periodically or non-periodically.

For example, the output unit 24 outputs, for example, the facility information of the service facility determined by the information processing device 10 to the occupants in the vehicle cabin of the vehicle 20. For example, the output unit 24 includes a car navigation device. For example, the output unit 24 includes an output device such as a liquid crystal monitor that constitutes the car navigation device. The car navigation device constituting the output unit 24 outputs, for example, information using at least either of an image and a sound.

The output unit 24 is not limited to this, and may include any output device that affects at least either of visual and auditory senses of the occupant of the vehicle 20. The output unit 24 may include, for example, any audio output device other than the car navigation device, which mainly affects the hearing of the occupant of the vehicle 20. The output unit 24 may include, for example, any image output device other than the car navigation device, which mainly affects the visual sense of the occupant of the vehicle 20.

The input unit 25 includes, for example, one or more input interfaces that receive an input operation by the occupant in response to the information output by the output unit 24 and acquire input information based on the input operation by the occupant. For example, the input unit 25 includes a car navigation device that constitutes the output unit 24. For example, the input unit 25 includes a touch screen provided integrally with the liquid crystal monitor constituting the car navigation device. The car navigation device constituting the input unit 25 receives, for example, the input operation by the occupant based on a touch operation of the occupant.

The input unit 25 is not limited to this, and may include any input interface capable of detecting the input operation by the occupant and acquiring the input information based on the input operation by the occupant. The input unit 25 may include, for example, a physical key, a capacitance key, and a microphone that accepts voice inputs.

The control unit 26 includes one or more processors. According to the embodiment, the "processor" is a general-purpose processor or a dedicated processor specialized for specific processing. However, the processor is not limited thereto. For example, the control unit 26 may include an electronic control unit (ECU). The control unit 26 is connected to each component constituting the vehicle 20 so as to be able to communicate with each other and controls the operation of the entire vehicle 20.

The control unit 26 uses the acquisition unit 23 to acquire the biometric information and the occupant information for each of the occupants of the vehicle 20. The control unit 26 transmits the biometric information and the occupant information of the occupants of the vehicle 20 acquired by the acquisition unit 23 to the information processing device 10 via the communication unit 21 and the network 30.

The control unit 26 receives the facility information of the service facility determined by the information processing device 10 from the information processing device 10 via the network 30 and the communication unit 21. The control unit 26 outputs the facility information of the service facility received from the information processing device 10 to the output unit 24. For example, when there is a plurality of candidates for the service facility determined by the information processing device 10, the control unit 26 lists on the output unit 24 the facility information of the service facilities determined. The control unit 26 transmits the facility information of the service facility selected by the occupant of the vehicle 20 using the input unit 25 among the candidates for the service facility displayed in the list to the information processing device 10 via the communication unit 21 and the network 30.

The control unit 26 receives route information to the service facility determined by the information processing device 10 from the information processing device 10 via the network 30 and the communication unit 21. The control unit 26 receives information on the autonomous driving state, described later, determined by the information processing device 10 from the information processing device 10 via the network 30 and the communication unit 21. The control unit 26 executes vehicle control for the vehicle 20 based on the route information to the service facility received from the information processing device 10 and the information on the autonomous driving state described later. In the present specification, the "vehicle control" includes, but is not limited to, autonomous driving to the service facility serving as a destination, for example.

Next, the configuration of the information processing device 10 included in the information processing system 1 will be mainly described. As shown in FIG. 2, the information processing device 10 includes a communication unit 11, a storage unit 12, and a control unit 13.

The communication unit 11 includes a communication module connected to the network 30. For example, the communication unit 11 may include a communication module compatible with mobile communication standards such as 4G and 5G or the Internet standards. According to the embodiment, the information processing device 10 is connected to the network 30 via the communication unit 11. The communication unit 11 transmits and receives various types of information via the network 30.

The storage unit 12 is, for example, a semiconductor memory, a magnetic memory, or an optical memory. However, the storage unit 12 is not limited to these memories. The storage unit 12 may function as, for example, a main storage device, an auxiliary storage device, or a cache memory. The storage unit 12 stores any information used for the operation of the information processing device 10. For example, the storage unit 12 may store a system program, an application program, and various types of information received by the communication unit 11. The information stored in the storage unit 12 may be updatable with information received from the network 30 via the communication unit 11, for example.

The control unit 13 includes one or more processors. According to the embodiment, the "processor" is a general-purpose processor or a dedicated processor specialized for specific processing. However, the processor is not limited thereto. The control unit 13 is connected to each of the components constituting the information processing device 10 so as to be able to communicate with each other and controls the operation of the entire information processing device 10.

The control unit 13 acquires the biometric information and the occupant information of the occupants of the vehicle 20. For example, the control unit 13 receives the biometric information and the occupant information acquired by the acquisition unit 23 of the vehicle 20 from the vehicle 20 via the network 30 and the communication unit 11. The control unit 13 estimates the state information of the occupants based on the acquired biometric information of the occupants.

The control unit 13 compares the estimated state information of the occupants and the acquired occupant information of the occupants with the past data for other occupants in which the state information and the occupant information are associated with the facility information of the service facilities used. Thereby, the control unit 13 determines service facility fit for the occupant of the vehicle 20. The control unit 13 may receive the past data from any other external device via the network 30 and the communication unit 11 and store the past data in the storage unit 12.

FIG. 3 is a first diagram illustrating a first example of a process executed by the control unit 13 of the information processing device 10 shown in FIG. 2. FIG. 4 is a second diagram illustrating the first example of the process executed by the control unit 13 of the information processing device 10 shown in FIG. 2. FIG. 4 shows an example of the past data. The first example of the process executed by the control unit 13 will be described more specifically with reference to FIGS. 3 and 4.

In the first example of the process executed by the control unit 13, a service facility fit for the occupant of the vehicle 20 is determined based on the biometric information and the occupant information acquired by the control unit 13. Although four vehicles A1, A2, A3, and A4 are shown in FIG. 3, the number of vehicles 20 corresponding to the service facilities determined by the control unit 13 does not have to be four. Similarly, although FIG. 4 shows four vehicles B1, B2, B3, and B4, the number of vehicles 20 included in the past data does not have to be four.

The control unit 13 acquires the information indicating one adult male as the occupant information of the occupant of the vehicle A1. The control unit 13 estimates information indicating the degree of drowsiness 90 as the state information of the occupant based on the acquired biometric information of the occupant of the vehicle A1. The control unit 13 compares the estimated state information of the occupant indicating the degree of drowsiness 90 and the acquired occupant information of the occupant indicating one adult male with the past data. More specifically, the control unit 13 compares the information about the occupant of the vehicle A1 with the past data for another occupant of the vehicle B2. In the past data for the other occupant of the vehicle B2, the occupant information includes the information indicating one adult male. The state information includes information indicating the degree of drowsiness 85. In this way, the control unit 13 executes the comparison process while referring to the past data of the vehicle B2 including information similar to the occupant information and the state information of the occupant of the vehicle A1.

In such a comparison process, the control unit 13 refers to information indicating a capsule hotel used by the other occupant of the vehicle B2, which is associated with the information similar to the occupant information and the state information of the occupant of the vehicle A1, as the facility information of the service facility. Thereby, the control unit 13 determines the capsule hotel as a service facility fit for the occupant of the vehicle A1.

The control unit 13 acquires the information indicating two adults and two children as the occupant information of the occupants of the vehicle A2. The control unit 13 estimates information indicating the degree of drowsiness 90 as the state information of the occupant based on the acquired biometric information of the occupant of the vehicle A2. When there is a plurality of occupants as in the case of the vehicle A2, the control unit 13 may calculate the average value of the state information estimated based on the biometric information of each of the occupants. That is, the state information indicating the degree of drowsiness 90, which is obtained in relation to the vehicle A2, may be an average value calculated for the plurality of occupants.

The control unit 13 compares the estimated state information of the occupant indicating the degree of drowsiness 90 and the acquired occupant information of the occupant indicating two adults and two children with the past data. More specifically, the control unit 13 compares the information about the occupants of the vehicle A2 with past data for other occupants of the vehicle B4. In the past data for the other occupants of the vehicle B4, the occupant information includes the information indicating two adults and one child. The state information includes information indicating the degree of drowsiness 90. Similar to the case of the vehicle A2, the state information obtained in relation to the vehicle B4 and indicating the degree of drowsiness 90 may be an average value calculated for the occupants. As described above, the control unit 13 executes the comparison process while referring to the past data of the vehicle B4 including information similar to the occupant information and the state information of the occupants of the vehicle A2.

In such a comparison process, the control unit 13 refers to information indicating a family-friendly hotel used by the other occupants of the vehicle B4, which is associated with the information similar to the occupant information and the state information of the occupants of the vehicle A2, as the facility information of the service facility. Thereby, the control unit 13 determines the family-friendly hotel as a service facility fit for the occupants of the vehicle A2.

As described above, for example, when the occupant information includes the number of occupants, the control unit 13 determines a service facility fit for the occupants of the vehicle 20 based on the number of occupants of the vehicle 20. More specifically, as can be easily understood by comparing the case of the vehicle A1 and the case of the vehicle A2 in FIG. 3, when the same state information is obtained but the number of occupants included in the occupant information is different, the control unit 13 determines different service facilities for the occupant of the vehicle A1 and the occupants of the vehicle A2 as the service facilities fit for the occupants of vehicle 20.

The control unit 13 acquires the information indicating one adult female as the occupant information of the occupant of the vehicle A3. The control unit 13 estimates information indicating the degree of fatigue 90 as the state information of the occupant based on the acquired biometric information of the occupant of the vehicle A3. The control unit 13 compares the estimated state information of the occupant indicating the degree of fatigue 90 and the acquired occupant information of the occupant indicating one adult female with the past data. More specifically, the control unit 13 compares the information about the occupant of the vehicle A3 with the past data for another occupant of the vehicle B1. In the past data for the other occupant of the vehicle B1, the occupant information includes the information indicating one adult female. The state information includes information indicating the degree of fatigue 85. In this way, the control unit 13 executes the comparison process while referring to the past data of the vehicle B1 including information similar to the occupant information and the state information of the occupant of the vehicle A3.

In such a comparison process, the control unit 13 refers to information indicating a massage shop used by the other occupant of the vehicle B1, which is associated with the information similar to the occupant information and the state information of the occupant of the vehicle A3, as the facility information of the service facility. Thereby, the control unit 13 determines the massage shop as a service facility fit for the occupant of the vehicle A3.

The control unit 13 acquires the information indicating two adults as the occupant information of the occupants of the vehicle A4. The control unit 13 estimates information indicating the degree of lack of exercise 90 as the state information of the occupants based on the acquired biometric information of the occupants of the vehicle A4. In the case of the vehicle A4, as in the case of the vehicle A2, the state information indicating the degree of lack of exercise 90 may be an average value calculated for the occupants.

The control unit 13 compares the estimated state information of the occupant indicating the degree of lack of exercise 90 and the acquired occupant information of the occupant indicating two adults with the past data. More specifically, the control unit 13 compares the information about the occupants of the vehicle A4 with the past data for other occupants of the vehicle B3. In the past data for the other occupants of the vehicle B3, the occupant information includes the information indicating three adults. The state information includes information indicating the degree of lack of exercise 90. Similar to the case of the vehicle A4, the state information obtained in relation to the vehicle B3 and indicating the degree of lack of exercise 90 may be an average value calculated for the occupants. As described above, the control unit 13 executes the comparison process while referring to the past data of the vehicle B3 including information similar to the occupant information and the state information of the occupants of the vehicle A4.

In such a comparison process, the control unit 13 refers to information indicating a fitness club used by the other occupants of the vehicle B3, which is associated with the information similar to the occupant information and the state information of the occupants of the vehicle A4, as the facility information of the service facility. Thereby, the control unit 13 determines the fitness club as the service facility fit for the occupants of the vehicle A4.

The control unit 13 may notify the occupant of the vehicle 20 of the facility information of the service facility determined as described above. For example, the control unit 13 transmits the facility information of the determined service facility to the vehicle 20 via the communication unit 11 and the network 30. For example, the control unit 13 may determine whether the state information of the occupant has reached a threshold value in the notification to the occupant of the vehicle 20. That is, when the control unit 13 determines that the state information of the occupant has reached the threshold value, the control unit 13 may notify the occupant of the vehicle 20 of the facility information of the determined service facility. In the present specification, the "threshold value" includes, for example, a value of the state information that is appropriately determined within a numerical range, with respect to the state information represented by the numerical range. Such a threshold value may be appropriately set in advance when the information processing system 1 is constructed, or may be appropriately set by the occupant of the vehicle 20. When there is a plurality of occupants of the vehicle 20, the control unit 13 may compare the average value of the state information for the occupants with the threshold value.

As shown in FIG. 3, it has been stated that the control unit 13 determines one service facility for the occupant of the vehicle 20, but the present disclosure is not limited to this. The control unit 13 may determine a plurality of candidates for the service facility fit for the occupant of the vehicle 20. The control unit 13 may notify the occupant of the vehicle 20 of the facility information of each of the determined service facilities. For example, the control unit 13 transmits the facility information of each of the determined service facilities to the vehicle 20 via the communication unit 11 and the network 30.

For example, the control unit 13 receives the facility information of the service facility selected by the occupant using the input unit 25 of the vehicle 20 among the determined candidates for the service facility, from the vehicle 20 via the network 30 and the communication unit 11. The control unit 13 may determine the route information to the service facility based on the facility information of the service facility received from the vehicle 20. The control unit 13 may provide the determined route information to the vehicle 20. For example, the control unit 13 may transmit the determined route information to the vehicle 20 via the communication unit 11 and the network 30.

FIG. 5 is a diagram illustrating a second example of the process executed by the control unit 13 of the information processing device 10 shown in FIG. 2. The second example of the process executed by the control unit 13 will be described more specifically with reference to FIG. 5.

In the second example of the process executed by the control unit 13, the control unit 13 may determine the information on the autonomous driving state that matches the state information of the occupants and provide it to the vehicle 20. For example, the control unit 13 may transmit the determined information on the autonomous driving state to the vehicle 20 via the communication unit 11 and the network 30. In the present specification, the "information on the autonomous driving state" includes speed, acceleration, angular velocity, shift lever operation, steering operation, traveling lane, and the like of the vehicle 20. Although three vehicles C1, C2, and C3 are shown in FIG. 5, the number of vehicles 20 corresponding to the information on the autonomous driving state determined by the control unit 13 does not have to be three.

The control unit 13 estimates information indicating the degree of drowsiness 90 as the state information of the occupants of the vehicle C1. At this time, the control unit 13 determines the information on the autonomous driving state that matches the estimated state information of the occupants indicating the degree of drowsiness 90. For example, the control unit 13 determines the information on the autonomous driving state indicating low speed and low acceleration and provides the information to the vehicle C1 so that the occupants of the vehicle C1 having a high degree of drowsiness can be provided with stable driving of the vehicle C1.

The control unit 13 estimates the information indicating the degree of fatigue 90 as the state information of the occupants of the vehicle C2. At this time, the control unit 13 determines the information on the autonomous driving state that matches the estimated state information of the occupants indicating the degree of fatigue 90. For example, the control unit 13 determines the information on the autonomous driving state indicating low acceleration and provides the information to the vehicle C2 so that the occupants of the vehicle C2 having a high degree of fatigue can be provided with relatively stable driving of the vehicle C2.

The control unit 13 estimates information indicating the degree of lack of exercise 90 as the state information of the occupants of the vehicle C3. At this time, the control unit 13 determines the information on the autonomous driving state that matches the estimated state information of the occupants indicating the degree of lack of exercise 90. For example, the control unit 13 determines the information on the autonomous driving state indicating speed limit and provides the information to the vehicle C3, in order to enable the occupants of the vehicle C3 having a high degree of lack of exercise to exercise in the facility at an earliest possible stage.

Figure 6:
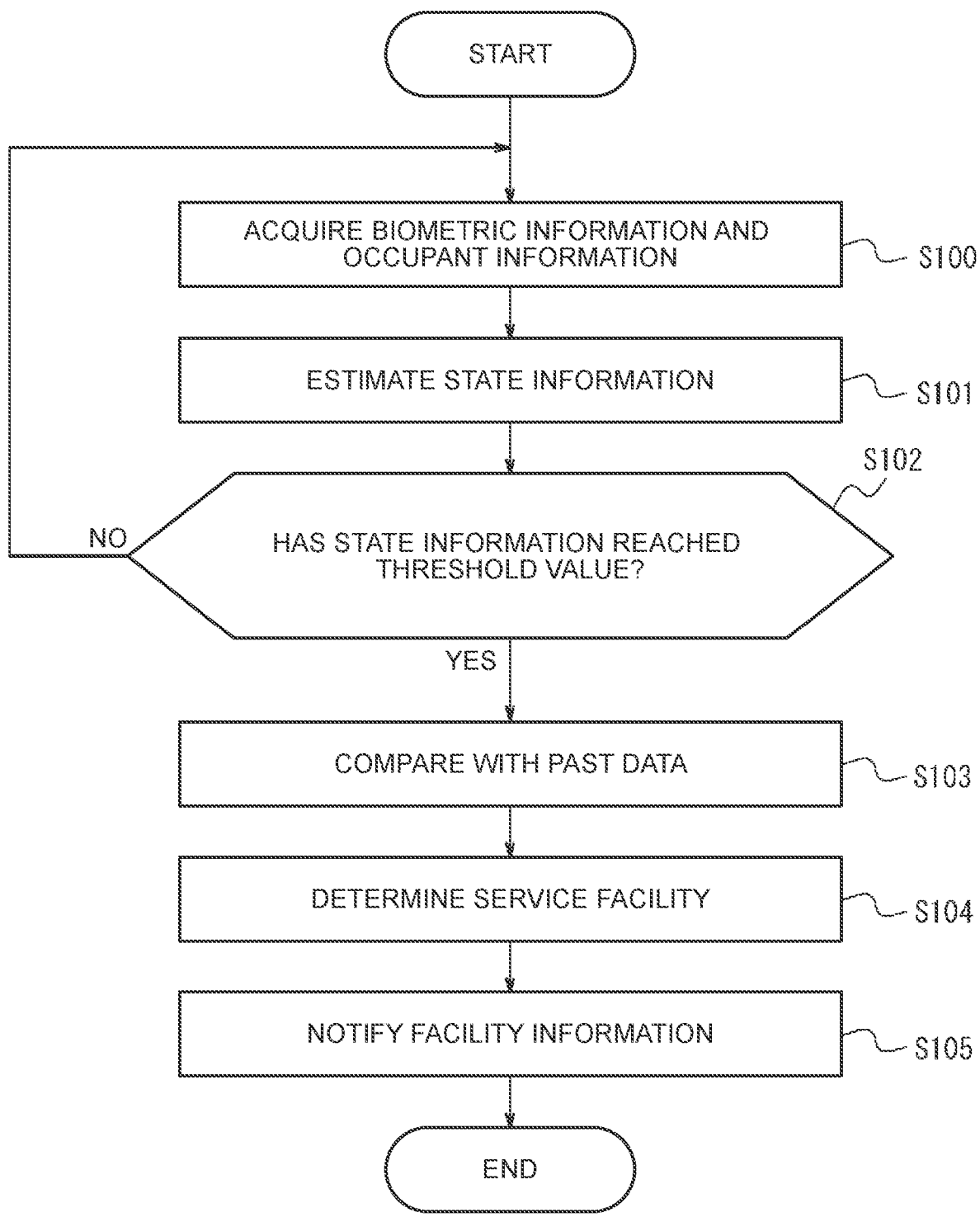
FIG. 6 is a flowchart illustrating a first example of an information processing method executed by the information processing device shown in FIG. 1.

Next, an information processing method executed by the control unit 13 of the information processing device 10 according to the embodiment will be described with reference to FIGS. 6 and 8. FIG. 6 is a flowchart illustrating a first example of the information processing method executed by the information processing device 10 shown in FIG. 1. In the first example of the information processing method, an example of a basic flow of the process executed by the control unit 13 of the information processing device 10 will be described.

In step S100, the control unit 13 acquires the biometric information and the occupant information of the occupant of the vehicle 20. For example, the control unit 13 receives the biometric information and the occupant information acquired by the acquisition unit 23 of the vehicle 20 from the vehicle 20 via the network 30 and the communication unit 11.

In step S101, the control unit 13 estimates the state information of the occupant based on the biometric information acquired in step S100.

In step S102, the control unit 13 determines whether the state information estimated in step S101 has reached the threshold value. When the control unit 13 determines that the state information has reached the threshold value, the control unit 13 executes the process of step S103. When the control unit 13 determines that the state information has not reached the threshold value, the control unit 13 executes the process of step S100.

In step S103, when the control unit 13 determines that the state information has reached the threshold value in step S102, the control unit 13 compares the state information estimated in step S101 and the occupant information acquired in step S100 with the past data for other occupants, in which the state information and the occupant information are associated with the facility information of the service facility used.

In step S104, the control unit 13 determines a service facility fit for the occupant of the vehicle 20 based on the comparison process in step S103.

In step S105, the control unit 13 notifies the occupant of the vehicle 20 of the facility information of the service facility determined in step S104. For example, the control unit 13 transmits the facility information of the service facility determined in step S104 to the vehicle 20 via the communication unit 11 and the network 30.

Figure 7:
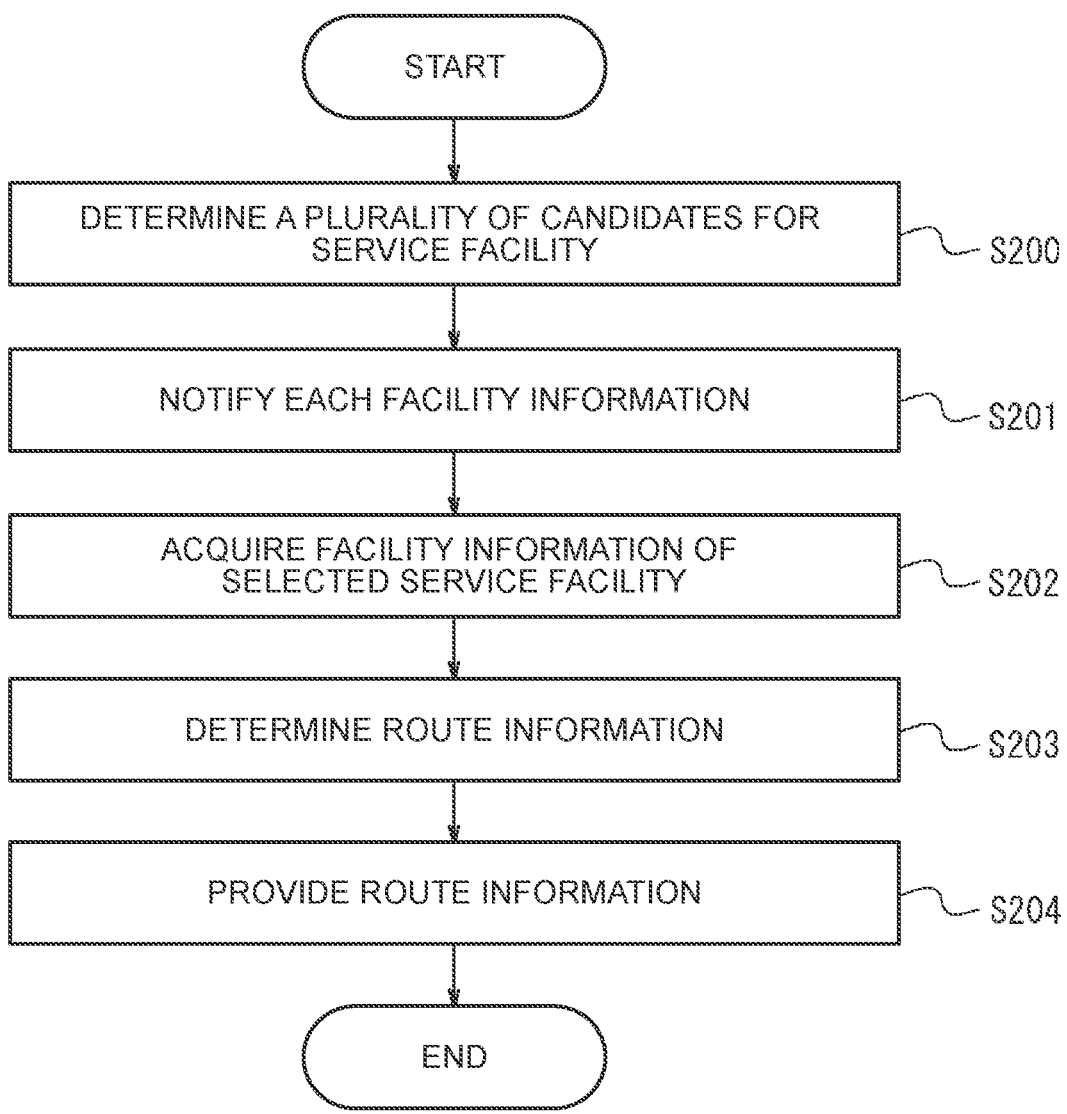
FIG. 7 is a flowchart illustrating a second example of the information processing method executed by the information processing device shown in FIG. 1.

FIG. 7 is a flowchart illustrating a second example of the information processing method executed by the information processing device 10 shown in FIG. 1. FIG. 7 shows an example of the process executed by the control unit 13 at the determination process and the subsequent processes when a plurality of candidates for the service facility are determined in step S104 of FIG. 6.

In step S200, the control unit 13 determines the candidates for the service facility fit for the occupant of the vehicle 20.

In step S201, the control unit 13 notifies the occupant of the vehicle 20 of the facility information of each of the service facilities determined in step S200. For example, the control unit 13 transmits the facility information of each of the service facilities determined in step S200 to the vehicle 20 via the communication unit 11 and the network 30.

In step S202, the control unit 13 acquires the facility information of the service facility selected by the occupant using the input unit 25 of the vehicle 20 among the candidates for the service facility determined in step S200. For example, the control unit 13 receives such facility information of the service facility from the vehicle 20 via the network 30 and the communication unit 11.

In step S203, the control unit 13 determines the route information to the service facility based on the facility information of the service facility acquired in step S202.

In step S204, the control unit 13 provides the vehicle 20 with the route information determined in step S203. For example, the control unit 13 transmits the route information determined in step S203 to the vehicle 20 via the communication unit 11 and the network 30.

Figure 8:
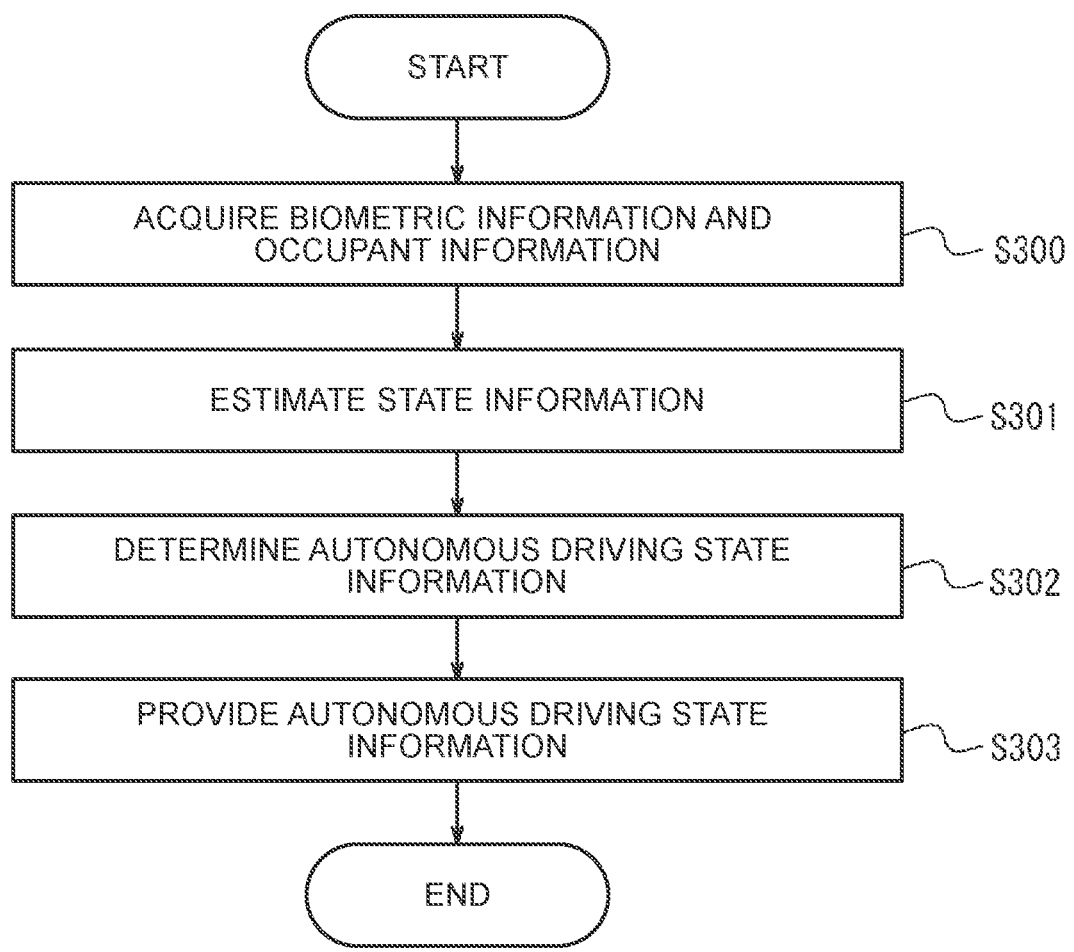
FIG. 8 is a flowchart illustrating a third example of the information processing method executed by the information processing device shown in FIG. 1.

FIG. 8 is a flowchart illustrating a third example of the information processing method executed by the information processing device 10 shown in FIG. 1. FIG. 8 shows an example of the process executed by the control unit 13 in parallel with or at a different timing from the subsequent flow of FIG. 6 when the state information is estimated in step S101 of FIG. 6.

In step S300, the control unit 13 acquires the biometric information and the occupant information of the occupant of the vehicle 20. For example, the control unit 13 receives the biometric information and the occupant information acquired by the acquisition unit 23 of the vehicle 20 from the vehicle 20 via the network 30 and the communication unit 11.

In step S301, the control unit 13 estimates the state information of the occupant based on the biometric information acquired in step S300.

In step S302, the control unit 13 determines the information on the autonomous driving state that matches the state information estimated in step S301.

In step S303, the control unit 13 provides the vehicle 20 with the information on the autonomous driving state determined in step S302. For example, the control unit 13 transmits the information on the autonomous driving state determined in step S302 to the vehicle 20 via the communication unit 11 and the network 30.

According to the embodiment as described above, the service facility to be proposed to the occupant of the vehicle 20 can be optimized based on the biometric information of the occupant. For example, the information processing device 10 can determine the service facility fit for the state of the occupant by estimating the state information of the occupant based on the acquired biometric information. In addition, the information processing device 10 can accurately determine a service facility fit for the occupant of the vehicle 20 by comparing the estimated state information and the acquired occupant information with the past data. The information processing device 10 determines the service facility fit for the occupant of the vehicle 20 based not only on the biometric information of the occupant but also on the occupant information of the occupant, so that the information processing device 10 can more accurately determine the service facility compared with the case of determining based only on the biometric information of the occupant. Thus, potential demand regarding service content that the occupant desires to be provided with is satisfied, the occupant receiving the notification of the facility information of the service facility determined by the information processing device 10 and receiving the guidance to the service facility from the vehicle 20. Therefore, the satisfaction level of the occupant of the vehicle 20 is improved.

For example, the information processing device 10 can propose an accommodation facility such as a capsule hotel to an occupant with a high degree of drowsiness in response to the potential demand of the occupant for sleep, so as to satisfy the demand of the occupant. For example, the information processing device 10 can propose a healing facility such as a massage shop to an occupant with a high degree of fatigue in response to the potential demand of the occupant for healing his/her fatigue, so as to satisfy the demand of the occupant. For example, the information processing device 10 can propose a health facility such as a fitness club to an occupant with a high degree of lack of exercise in response to the potential demand of the occupant for elimination of the lack of exercise, so as to satisfy the demand of the occupant.

The information processing device 10 can appropriately determine the service facility in accordance with the number of occupants by determining the service facility fit for the occupant based on the number of occupants of the vehicle 20. Thereby, similarly to the above, the potential demand of the occupant regarding the service content is satisfied, which improves the satisfaction level of the occupant of the vehicle 20.

The information processing device 10 notifies the occupant of the determined facility information of the service facility when determining that the occupant state information of the vehicle 20 has reached the threshold value, so that the information processing device 10 can notify the occupant of the facility information of the service facility at the optimum timing in accordance with the state of the occupant of the vehicle 20. For example, the information processing device 10 can notify the occupant of the facility information of the service facility at a timing when the occupant of the vehicle 20 potentially desires to receive the service. Thus, similarly to the above, the potential demand of the occupant regarding the timing at which the service is provided is satisfied, which improves the satisfaction level of the occupant of the vehicle 20.

When there is a plurality of occupants of the vehicle 20, the information processing device 10 compares the average value of the state information of the occupants with the threshold value, so that the information processing device 10 can notify the occupant of the facility information of the service facility at an appropriate timing that suits the states of the occupants of the vehicle 20 in an average manner. Thus, similarly to the above, the potential demands of the occupants regarding the timing at which the service is provided are satisfied in an average manner, which improves the satisfaction level of the occupants of the vehicle 20.

The information processing device 10 provides the vehicle 20 with the route information to the service facility selected by the occupant of the vehicle 20, so that the information processing device 10 can execute vehicle control on the vehicle 20 to the service facility explicitly desired by the occupant. The vehicle 20 can appropriately guide the occupant to the service facility selected by the occupant.

The information processing device 10 determines the information on the autonomous driving state that matches the state information of the occupant and provides the information to the vehicle 20, so that the vehicle 20 can realize the optimum autonomous driving state that matches the state of the occupant. Thus, stress of the autonomous driving that the occupant of the vehicle 20 feels is relieved, which improves the comfort of the occupant with the autonomous driving of the vehicle 20.

Since the state information includes the degree of drowsiness of the occupant of the vehicle 20, the information processing device 10 can optimize the service facility to be proposed to the occupant of the vehicle 20 based on the degree of drowsiness of the occupant of the vehicle 20. This satisfies the potential demand of the occupant for the service content that the occupant desires to receive based on the degree of drowsiness. Thus, the satisfaction level of the occupant of the vehicle 20 is improved.

The information processing device 10 can accurately determine a service facility fit for the occupant by comparing the estimated state information and the acquired occupant information with the past data including big data.

Although the present disclosure has been described above based on the drawings and the embodiments, it should be noted that those skilled in the art can easily make various modifications and alterations thereto based on the present disclosure. It should be noted, therefore, that these modifications and alterations are within the scope of the present disclosure. For example, the functions included in the configurations, steps, etc. can be rearranged so as not to be logically inconsistent, and a plurality of configurations, steps, etc. can be combined into one or divided.

For example, at least a part of the processing operations executed by the information processing device 10 in the above embodiment may be executed by the vehicle 20. For example, instead of the information processing device 10, the vehicle 20 itself may execute the processing operations above related to the information processing device 10. At least a part of the processing operations executed by the vehicle 20 may be executed by the information processing device 10.

For example, a general-purpose electronic device such as a smartphone or a computer may function as the information processing device 10 according to the above embodiment. Specifically, a program including processing content for realizing each function of the information processing device 10 and the like according to the embodiment is stored in a memory of the electronic device, and the program is read and executed by the processor of the electronic device. Thus, the disclosure according to the embodiment can also be realized as a program that can be executed by the processor. Alternatively, the disclosure according to the embodiment can also be realized as a non-transitory computer-readable medium that stores a program executable by one or more processors to cause the information processing device 10 etc. according to the embodiment to execute each function. It should be understood that the above configurations are also included in the scope of the present disclosure.

For example, the information processing device 10 described in the above embodiment may be mounted on the vehicle 20. With the configuration above, the information processing device 10 may directly perform information communication with the vehicle 20 without the network 30.

In the above embodiment, it has been stated that the information processing device 10 provides the vehicle 20 with the information determined by the information processing device 10, such as the facility information of the service facility and the route information to the service facility, but the present disclosure is not limited to this. The information processing device 10 may provide the terminal device of the occupant of the vehicle 20, in place of or in addition to the vehicle 20, with the above types of information. With the configuration above, the information processing system 1 may include the terminal device of the occupant of the vehicle 20 in addition to the information processing device 10 and the vehicle 20.

In the above embodiment, it has been stated that the information processing device 10 notifies the occupant of the facility information of the determined service facility when determining that the state information of the occupant has reached the threshold value, but the present disclosure is not limited to this. For example, the information processing device 10 may omit the determination process in step S102 of FIG. 6.

In the above embodiment, it has been described that the past data includes, for example, big data, but the present disclosure is not limited to this. The past data may include any data in which the state information and the occupant information obtained in the past in relation to the other occupants are associated with the facility information of the service facility used by the other occupants.

In the above embodiment, the information processing device 10 has been described as acquiring the past data from any other external device via the network 30 and the communication unit 11, but the present disclosure is not limited to this. The information processing device 10 itself may generate the past data in which the state information and the occupant information obtained in the past in relation to other occupants are associated with the facility information of the service facility used by the other occupants and store the past data in the storage unit 12.

For example, the information processing device 10 is not limited to the above embodiment. The information processing device 10 may determine the service facility fit for the occupant, based on the date and time when the vehicle 20 is traveling, the position information of the vehicle 20 acquired by the acquisition unit 23 of the vehicle 20, and the like, in addition to the biometric information and the occupant information of the occupant of the vehicle 20.

What is claimed is:

1. An information processing device comprising:
   a control unit configured to:
   acquire biometric information and occupant information of an occupant of a vehicle,
   estimate state information of the occupant based on the acquired biometric information,
   compare the estimated state information and the acquired occupant information with past data for another occupant in which the state information and the occupant information are associated with facility information of a service facility used to determine a service facility fit for the occupant,
   determine information on an autonomous driving state that matches the state information, and
   provide the information on the autonomous driving state to the vehicle, wherein the estimated state information includes a degree of drowsiness and a degree of fatigue, the occupant information includes a quantity of occupants,
   the control unit is configured to:
   determine a first service facility when the state information of the occupant is a first occupant state and the quantity of occupants is a first value, and determine a second service facility when the state information of the occupant is the first occupant state and the quantity of occupants is a second value,
   propose an accommodation facility including a capsule hotel to an occupant with a high degree of drowsiness and the quantity of less than two,
   propose the accommodation facility including a family hotel to an occupant with the high degree of drowsiness and the quantity of more than one,
   propose a healing facility including a massage shop to an occupant with a high degree of fatigue,
   determine the information on the autonomous driving state as a first autonomous driving state for the occupant with the high degree of drowsiness and the quantity of less than two and for the occupant with the high degree of drowsiness and the quantity of more than one, and
   determine the information on the autonomous driving state as a second autonomous driving state different from the first autonomous driving state for the occupant with the high degree of fatigue, and
   the vehicle is configured to execute vehicle control to control the vehicle to drive to the service facility.

2. The information processing device according to claim 1, wherein when the control unit determines that the state information has reached a threshold value, the control unit notifies the occupant of the facility information of the determined service facility.

3. The information processing device according to claim 2, wherein when there is a plurality of occupants, the control unit compares an average value of the state information of the occupants with the threshold value.

4. The information processing device according to claim 2, wherein the control unit is configured to:
   determine a plurality of candidates for the service facility fit for the occupant, and
   provide the vehicle with route information to a service facility selected by the occupant among the determined candidates for the service facility.

5. The information processing device according to claim 1, wherein
   the first autonomous driving state includes a speed lower than a predetermined speed, and
   the second autonomous state includes an acceleration lower than a predetermined acceleration.

6. An information processing system, comprising:
   the information processing device according to claim 1; and
   the vehicle that provides the information processing device with the biometric information and the occupant information.

7. A non-transitory computer readable medium storing a program that causes an information processing device to perform operations including:
   acquiring biometric information and occupant information of an occupant of a vehicle;
   estimating state information of the occupant based on the acquired biometric information;
   comparing the estimated state information and the acquired occupant information with past data for another occupant in which the state information and the occupant information are associated with facility information of a service facility used;
   determining a service facility fit for the occupant;
   determining information on an autonomous driving state that matches the state information, and
   providing the information on the autonomous driving state to the vehicle, wherein
   the estimated state information includes a degree of drowsiness and a degree of fatigue,
   the occupant information includes a quantity of occupants,
   the operations include:
   determining a first service facility when the state information of the occupant is a first occupant state and the quantity of occupants is a first value, and determine a second service facility when the state information of the occupant is the first occupant state and the quantity of occupants is a second value, proposing an accommodation facility including a capsule hotel to an occupant with a high degree of drowsiness and the quantity of less than two, proposing the accommodation facility including a family hotel to an occupant with the high degree of drowsiness and the quantity of more than one, proposing a healing facility including a massage shop to an occupant with a high degree of fatigue, determining the information on the autonomous driving state as a first autonomous driving state for the occupant with the high degree of drowsiness and the quantity of less than two and for the occupant with the high degree of drowsiness and the quantity of more than one, and determining the information on the autonomous driving state as a second autonomous driving state different from the first autonomous state for the occupant with the high degree of fatigue, and the vehicle is configured to execute vehicle control to control the vehicle to drive to the service facility.

8. The program according to claim 7, wherein the operations include:

determining whether the state information has reached a threshold value, and notifying the occupant of the facility information of the determined service facility when determining that the state information has reached the threshold value.

9. The program according to claim 8, wherein the operations include when there is a plurality of occupants, comparing an average value of the state information of the occupants with the threshold value.

10. The program according to claim 8, wherein the operations include:

determining a plurality of candidates for the service facility fit for the occupant, determining route information to a service facility selected by the occupant among the determined candidates for the service facility, and providing the vehicle with the determined route information.

11. The program according to claim 7, wherein the first autonomous driving state includes a speed lower than a predetermined speed, and the second autonomous driving state includes an acceleration lower than a predetermined acceleration.

12. A vehicle, comprising:

a control unit configured to:

acquire biometric information and occupant information of an occupant of the vehicle, estimate state information of the occupant based on the acquired biometric information, compare the estimated state information and the acquired occupant information with past data for another occupant in which the state information and the occupant information are associated with facility information of a service facility used to determine a service facility fit for the occupant, determine information on an autonomous driving state that matches the state information, and execute vehicle control to control the vehicle to drive to the service facility, wherein the estimated state information includes a degree of drowsiness and a degree of fatigue, the occupant information includes a quantity of occupants, and the control unit is configured to:

determine a first service facility when the state information of the occupant is a first occupant state and the quantity of occupants is a first value, and determine a second service facility when the state information of the occupant is the first occupant state and the quantity of occupants is a second value, propose an accommodation facility including a capsule hotel to an occupant with a high degree of drowsiness and the quantity of less than two, propose the accommodation facility including a family hotel to an occupant with the high degree of drowsiness and the quantity of more than one, propose a healing facility including a massage shop to an occupant with a high degree of fatigue, determine the information on the autonomous driving state as a first autonomous driving state for the occupant with the high degree of drowsiness and the quantity of less than two and for the occupant with the high degree of drowsiness and the quantity of more than one, and determine the information on the autonomous driving state as a second autonomous driving state different from the first autonomous driving state for the occupant with the high degree of fatigue.

13. The vehicle according to claim 12, wherein when the control unit determines that the state information has reached a threshold value, the control unit notifies the occupant of the facility information of the determined service facility.

14. The vehicle according to claim 13, wherein when there is a plurality of occupants, the control unit compares an average value of the state information of the occupants with the threshold value.

15. The vehicle according to claim 13, wherein the control unit is configured to:

determine a plurality of candidates for the service facility fit for the occupant, and determine route information to a service facility selected by the occupant among the determined candidates for the service facility.

16. He vehicle according to claim 12, wherein the first autonomous driving state includes a speed lower than a predetermined speed, and the second autonomous driving state includes an acceleration lower than a predetermined acceleration.

* * * * *